(12) United States Patent
King et al.

(10) Patent No.: US 7,094,323 B2
(45) Date of Patent: Aug. 22, 2006

(54) PROCESS ANALYZER FOR MONITORING ELECTROCHEMICAL DEPOSITION SOLUTIONS

(75) Inventors: Mackenzie King, Southbury, CT (US); John Staples, Buffalo Grove, IL (US)

(73) Assignee: Advanced Technology Materials, Inc., Danbury, CT (US)

( * ) Notice: Subject to any disclaimer, the term of this patent is extended or adjusted under 35 U.S.C. 154(b) by 413 days.

(21) Appl. No.: 10/320,876

(22) Filed: Dec. 17, 2002

(65) Prior Publication Data

US 2003/0127324 A1 Jul. 10, 2003

(51) Int. Cl.
*G01N 27/413* (2006.01)
*G01N 27/416* (2006.01)

(52) U.S. Cl. .......................... 204/434; 204/416; 205/81

(58) Field of Classification Search ................ 204/416, 204/434; 205/81
See application file for complete search history.

(56) References Cited

U.S. PATENT DOCUMENTS 5,635,043 A * 6/1997 Tur yan et al. ............. 204/412
6,280,602 B1 8/2001 Robertson
6,365,033 B1 4/2002 Graham et al.

OTHER PUBLICATIONS

Wojciechowski et al. ("Square-wave anodic stripping voltammetry of lead and cadmium at cylindrical graphite fiber microelectrodes with in situ plated mercury films," Analytica Chimica Acta, 249 (1991) 433-445.*
Product description of MVA-3 voltammetry system by Metrohm. Downloaded on May 11, 2005 from www.metrohm.com/products/06/mva/mva03/mva03.html.*
Product description of 731 Relay Box by Metrohm. Downloaded on May 11, 2005 from www.metrohm.com/products/05/acc/731/731.html.*
Product description of 772 Pump Unit by Metrohm. Downloaded on May 11, 2005 from www.metrohm.com/products/05/acc/772/772.html.*
Product description of Titrando PC Control by Metrohm. Downloaded on May 11, 2005 from www.metrohm.com/products/control/pc/pc.html.*
Product description of Titrando PC Control by Metrohm. Downloaded on May 11, 2005 from www.metrohm.com/products/units/800/800.html.*
Universal Serial Bus—Wikipedia, the free encyclopedia downloaded from en.wikipedia.org/wiki/USB on May 11, 2005.*
Dennis Teach and John White Cyclic Pulse Voltammetric Stripping Analysis of Acid Copper Plating Baths, Apr. 1985, J. Electrochem. Soc. Electrochemical Science and Technology pp. 831-834.

* cited by examiner

*Primary Examiner*—Alex Noguerola
(74) *Attorney, Agent, or Firm*—Vincent K. Gustafson; Intellectual Property/Technology Law; Maggie Chappuis

(57) ABSTRACT

The present invention relates to a process analyzer for analyzing composition of sample electrochemical deposition solutions, comprising at least one microelectrode having a radius of not more than about 5 µm. The process analyzer preferably comprises: (1) two or more independent analytical modules for analyzing fluid samples, (2) a primary manifold communicatively connected to the analytical modules for introducing fluid samples thereinto, and (3) a computational device communicatively associated with the analytical modules for colleting and processing analytical data therefrom, and therefore can be used to conduct automatic and simultaneous analysis of two or more sample solutions.

20 Claims, 2 Drawing Sheets

PROCESS ANALYZER FOR MONITORING ELECTROCHEMICAL DEPOSITION SOLUTIONS

BACKGROUND OF THE INVENTION

1. Field of the Invention

The present invention in a broad aspect relates to analytical tools for monitoring electrochemical deposition (ECD) solutions, and more specifically to a process analyzer comprising microelectrodes for composition analysis of various metal electroplating solutions.

2. Related Art

Conventional ECD process analyzers use rotating disk electrodes (RDEs), for providing a well-defined flow of ECD solution towards the surface of such rotating disk electrodes, so as to provide stronger analytical signals (for example, the plating current).

When a rotating disk electrode rotates in a metal electroplating solution, it generates a flow pattern akin to a vortex that sucks the solution as well as analyte therein toward it. The layer of solution that is immediately adjacent to the surface of the rotating disk electrode behaves as if it were "stuck" to such electrode, i.e., while the bulk of the metal electroplating solution is being stirred vigorously by the rotating disk electrode, this thin layer of solution manages to cling to the surface of the electrode. Therefore, this thin layer of solution is generally referred to as "the stagnant layer" or "the boundary layer."

The metal electroplating solution and the analyte therein are conveyed to the surface of the rotating disk electrode by two types of motions: (1) the vortex flow generated by rotation of the RDE continuously brings fresh solution and analyte therein to the outer edge of the stagnant layer; and (2) the solution and analyte therein at the outer edge of the stagnant layer move across such stagnant layer via molecular diffusion. Therefore, the thinner the stagnant layer, the faster the solution and analyte therein can diffuse across it and reach the surface of the rotating disk electrode, and the higher the electric current measured by the RDE.

For generating a sufficiently thin stagnant layer, the RDE is generally operated at a rotating speed above 800 rpm, rendering such RDE prone to mechanical breakdown after continuous operation.

Moreover, the conventional RDE usually has a diameter of from about 1.5 mm to about 10 mm, in order to ensure structural integrity and reliability at such high rotating speed. Therefore, an ECD process analyzer that comprises a plurality of such conventional rotating disk electrodes is inevitable bulky in size.

Finally, when using such bulky ECD process analyzer, a large volume of sample metal electroplating solution has to be used in order to obtain sufficient analytical signals, generating a large amount of waste solution.

It would therefore be a significant advance in the art, and is accordingly an object of the present invention, to provide an ECD process analyzer comprising electrodes that are resistant to mechanical breakdown, small in size, and generating minimum amount of waste solution during solution analysis.

It is another object of the present invention to provide an automated analytical platform that comprises multiple analysis modules suitable for various kinds of fluidic analyses, preferably including at least one ECD process analyzer as described hereinabove.

Other objects and advantages will be more fully apparent from the ensuring disclosure and appended claims.

SUMMARY OF THE INVENTION

The present invention in a broad aspect relates to a process analyzer for analyzing composition of sample electrochemical deposition solutions, comprising at least one microelectrode having a radius of not more than 5 µm.

In a specific embodiment of the present invention, the process analyzer comprises one or more analytical modules for analyzing fluid samples, a primary manifold communicatively connected to the analytical modules for introducing fluid samples thereinto, and a computational device communicatively associated with the analytical modules for collecting and processing analytical data therefrom. Preferably, at least one of the analytical modules is a microelectrode cell that comprises a test electrode, a current source electrode, and a reference electrode, and the test electrode is a microelectrode that has a radius of not more than about 5 µm.

Additional aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
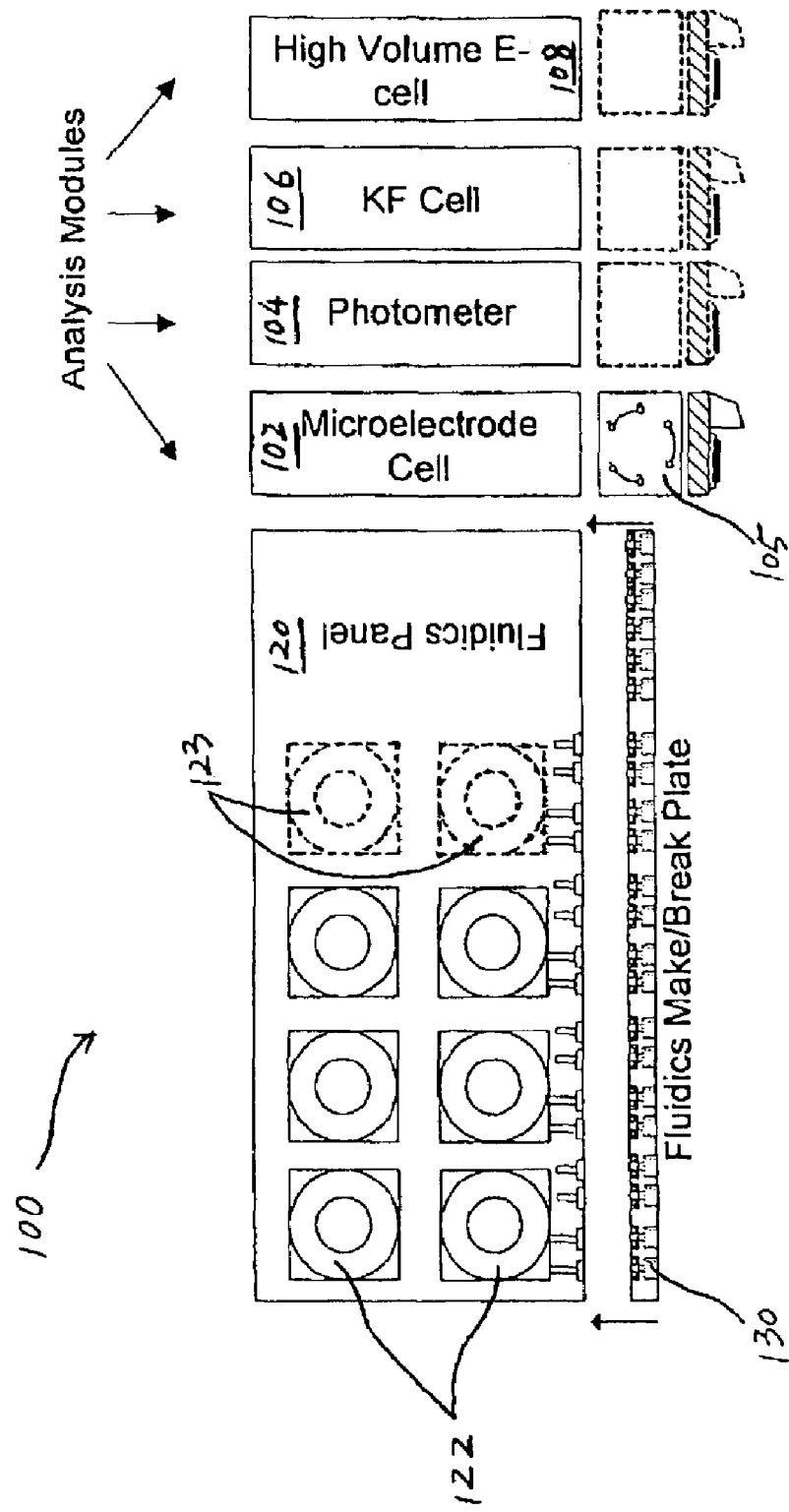
FIG. 1 is a top view of a process analyzer according to one embodiment of the present invention.

U.S. patent application Ser. No. 09/421,658 for "Method and Apparatus for Determination of Additives in Metal Plating Baths," as filed on Oct. 20, 1999 and issued as U.S. Pat. No. 6,280,602, discloses an analytical cell for conducting Pulsed Cyclic Galvanostatic Analysis (PCGA), the contents of which are incorporated hereby in their entirety for all purposes.

Conventional ECD process analyzers employ rotating disk electrodes in the PCGA cell to stir the electrolyte solution contained in such cell, for increasing the accuracy and consistency of measurements across PCGA cycles.

However, the rotating disk electrodes are vulnerable to mechanical breaking-down, when continuously operated at high rotating speed, as generally required by PCGA analysis.

Therefore, the present invention employs a microelectrode in place of the conventional rotating disk electrode in the ECD process analyzer. A microelectrode is defined hereby as an electrode having a radius of not more than 5 microns.

One major advantage of using such microelectrode is it is more resistant to mechanical breaking-down, in comparison to the conventional rotating disk electrode, because such microelectrode does not comprise moving parts and is devoid of rotatory motion.

Such microelectrode also allows for a much higher flux to the electrode surface, either by migration or diffusion, which provides sufficiently stronger analytical signals (such as current densities) than those provided by a rotating disk electrode.

For example, while using a microelectrode having a hemispherical tip and a radius of approximately 5 microns to obtain a steady state concentration profile in a concentration polarized system, the calculations show that the concentration of a target oxidized or reduced species at a distance of about 25 microns from the electrode is approximately 90% of the bulk concentration of said oxidized or reduced species. Such distance is only about ¼ of the thickness of the stagnant layer of a rotating disk electrode spinning at 955 rpm. The size of the microelectrode may be tailored to provide a much stronger flux to the electrode surface than the conventional rotating disk electrode by shrinking the radius. Similarly an array of various sized microelectrodes in the same electrochemical cell can be multiplexed in real time to vary the effective size and hence comparable rotation speed in real time.

The time required for a hemispherical microelectrode to reach steady state, after stepping the measurement potential to a given voltage, can be approximately calculated according to the following equation:

$$t_{ss} = 2500 \times r_0^2 / \pi D$$

wherein $t_{ss}$ is the time in which the electric current measured is only 2% greater than the steady state electric current, $r_0$ is the radius of the microelectrode, and D is the diffusion coefficient of the target species (typically $10^{-5}$ cm$^2$/s).

According to the above equation, when the radius of the microelectrode is about 5 microns, $t_{ss}$ is about 25 seconds, and when the radius is about 1 micron, $t_{ss}$ is about 1 second.

For very short duration experiments, which are possible with ultra-microelectrodes, on the order of less than 60 microseconds for a 5-micron electrode, where the diffusion layer is less than $r_o$, the current relationship is Cottrell like:

$$i = \frac{nFACoDo^{1/2}}{\pi^{1/2} t^{1/2}}$$

where D and C refer to concentration of the species of interest and that species diffusion coefficient.

The signal to noise for ultra-microelectrodes is enhanced over that of a conventional electrode by virtue of the fact that the low currents employed minimize uncompensated iR drops due to liquid resistance and two electrode systems may thus be used, minimizing stray current and environmental noise pickup.

Therefore, the use of a microelectrode with a radius of not more than 5 microns, preferably not more than 1 micron, not only provides a stronger analytical signal, but also enables quicker measurement of the sample solution, by allowing the steady state to be achieved faster, in comparison with use of the conventional rotating disk electrode.

Moreover, a process analyzer using microelectrodes can have significantly reduced size in comparison to one using conventional rotating disk electrodes, in light of the fact that the average diameter of the RDE is about 3 mm to about 10 mm, which is about 300 to about 5000 times larger than that of the microelectrode disclosed herein. Therefore, use of the microelectrodes enables such process analyzer to have much smaller footprint than that using conventional rotating disk electrode.

Further, multiple microelectrodes may be packed into a compact unit that comprises multiple analytical cells or modules for complimentary or simultaneous fluid measurements.

Finally, the microelectrodes allow measurement of fluid samples of very small volume, due to the small physical size of such electrodes, therefore resulting in less amount of waste.

In fact, the current analysis of organic additives in the high acid and low acid Viaform® chemistry, using a process analyzer comprising the microelectrodes, showed better results than the prior process analyzer that uses rotating disk electrodes.

The microelectrode as described hereinabove may comprise carbon fibers or platinum fibers. In a preferred embodiment, such microelectrode has a composite structure, with an inner electrically conductive metal core, and an outer dielectric layer formed by oxidization of a metal or metal alloy including metals such as tantalum, niobium, zirconium, hafnium, and titanium.

A PCGA-based process analyzer usually comprises a testing electrode, a current source electrode, and a reference electrode. It is preferred that at least the testing electrode is a microelectrode as defined hereinabove. It is more preferred that all the electrodes in such process analyzer are microelectrodes.

A preferred embodiment of the present invention relates to a multi-cell process analyzer, which comprises one or more analytical modules for analyzing fluid samples, a primary manifold communicatively connected to the analytical modules for introducing fluid samples thereinto, and a computational device communicatively associated with the analytical modules for collecting and processing analytical data therefrom.

FIG. 1 shows an example of such multi-cell process analyzer 100, which comprises four analytical modules 102, 104, 106, and 108 for analyzing various fluid samples. Specifically, analytical module 102 is a microelectrode cell that comprises at least one microelectrode as described hereinabove; analytical module 104 comprises a photometer for conducting spectroscopic analysis; analytical module 106 is a Karl Fischer cell for conducting Karl Fischer coulometry; and analytical module 108 is a high volume E-cell.

The analytical modules 102, 104, 106, and 108 are independent of one another, and they therefore are capable of conducting simultaneous fluid measurement or analysis. Such analytical modules are independently controlled by a microcontroller 105. A microcontroller is an inexpensive single-chip computer, which is capable of storing and running a program, and the PIC® microcontrollers manufactured by Microchip Technology (Chandler, Ariz.) are preferably employed for the purpose of controlling the analytical modules of the present invention. Additional analytical modules can be added for conducting PCGA, spectroscopic, potentiometric, and other traditional ECD solution measurements.

The process analyzer 100 also comprises a primary manifold 120, which is communicatively connected to the analytical modules for introducing fluid samples into such modules. The primary manifold 120 may comprise various pumps, valves, and fluidic tubing and pathway. Preferably, such primary manifold 120 employs variable volume displacement pumps, face-sealed valves, and pre-manufactured fluidic pathways, for the purpose of reducing the footprint of such manifold. It is also desirable to have such primary manifold 120 being mechanically attached to the analytical modules, so as to further reduce discrete plumbing required for conventional fluid manifolds used in ECD process analyzers.

Figure 2:
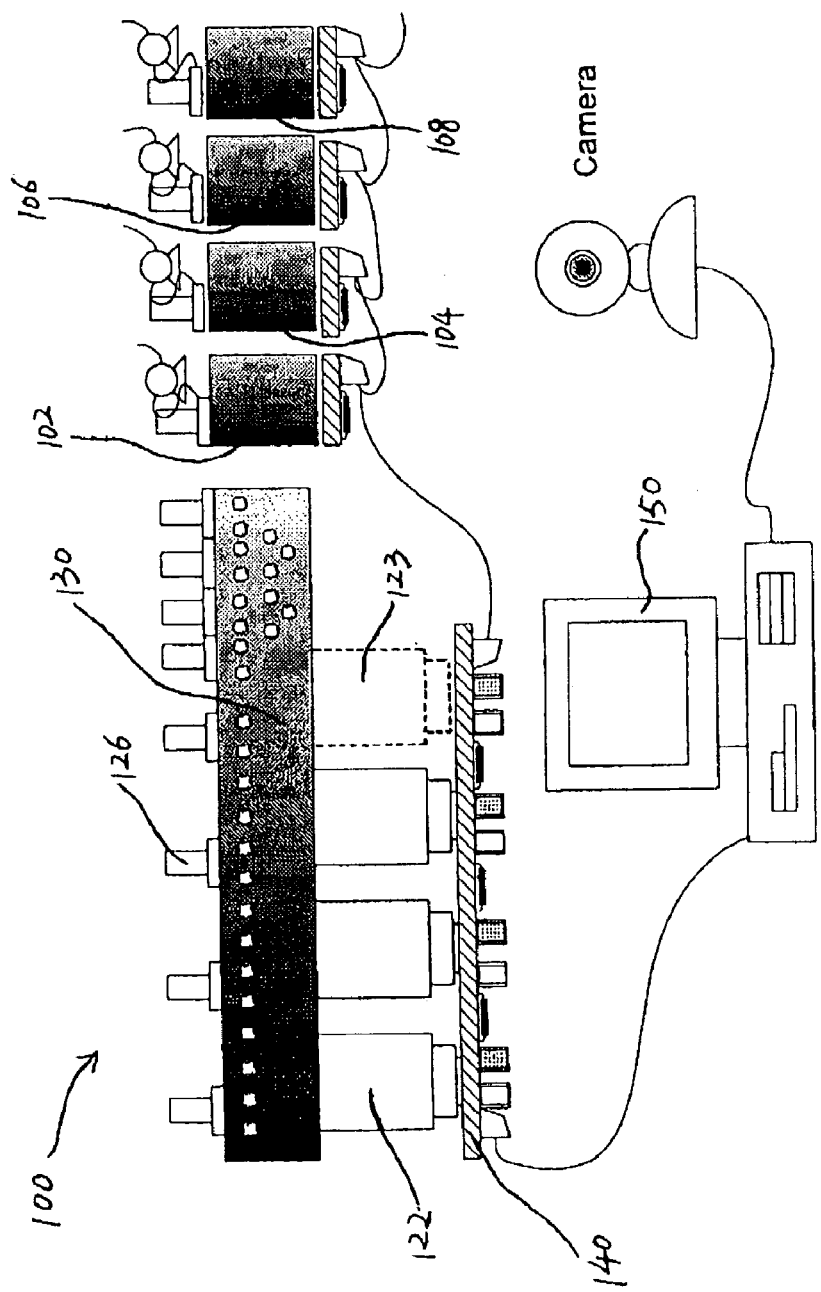
FIG. 2 is a side view of the process analyzer of FIG. 1.

For example the primary manifold 120 in FIG. 1 comprises 6 variable volume displacement pumps 122, with slots 123 for two more. It also comprises multiple valves 126 (as shown in FIG. 2), which may include face-sealed valves for pump flow control, two-way valves for CDA/N$_2$/water, and three-way valves for fluid diversion. Moreover, such primary manifold 120 comprises a make/break plate 130 having pre-manufactured fluid pathways thereon.

The process analyzer 100 further comprises a computational device 150 that is communicatively associated with the analytical modules for collecting and processing analytical data therefrom.

Such computational device 150 can be a microprocessor, or a personal computer, or an on-line data analysis system.

In one preferred embodiment of the present invention, the primary manifold 120 comprises a serial port 140 for connecting the microcontrollers 105 of the analytical modules with the computational device 150. One preferred serial port suitable for the purpose of practicing the present invention is an RS-485 driver board, which can be directly snapped onto the pumps 122. Such RS-485 driver board more preferably independently addresses each analytical module.

The computational device 150 preferably uses QNX software system for ensuring stability. It may comprise a low level interface to allow control of individual analytical modules for new applications, and a high level interface for processing and outputting analytical data to a central control network.

Such process analyzer as described hereinabove has significantly reduced size in comparison to conventional process analyzers. For example, a conventional copper ECD organic wet tray has a standard size of 8"×15"×17", and a copper ECD organic wet tray designed according to the present invention has a size of 4"×6"×7".

The decreased size of the process analyzer will significantly reduce sample and analyte consumption during the fluid analysis process.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A process analyzer for analyzing composition of sample electrochemical deposition solutions, said process analyzer comprising at least one microelectrode having a radius of not more than about 5 μm, wherein the microelectrode comprises a fiber selected from the group consisting of a carbon fiber and a platinum fiber, and further comprises a dielectric layer formed by oxidation of a metal or metal alloy including at least one metal selected from the group consisting of tantalum, niobium, zirconium, hafnium, and titanium.

2. The process analyzer of claim 1, wherein the microelectrode has a radius of not more than 1 μm.

3. The process analyzer of claim 1, wherein the microelectrode has a hemispherical tip.

4. The process analyzer of claim 1, wherein the microelectrode is non-rotational in relation to other components of said process analyzer.

5. The process analyzer of claim 1, comprising a test electrode, a current source electrode, and a reference electrode, wherein the test electrode is a microelectrode that has a radius of not more than about 5 μm and is non-rotational in relation to other components of said process analyzer.

6. The process analyzer of claim 1, comprising one or more analytical modules for analyzing fluid samples, a primary manifold communicatively connected to said analytical modules for introducing fluid samples thereinto, and a computational device communicatively associated with said analytical modules for collecting and processing analytical data therefrom.

7. The process analyzer of claim 6, comprising at least two analytical modules that are independent of one another, so that said process analyzer is capable of simultaneously analyzing at least two sample electrochemical deposition solutions.

8. The process analyzer of claim 7, wherein said one or more analytical modules are independently controlled by one or more microcontrollers.

9. The process analyzer of claim 6, wherein at least one of said analytical modules is a microelectrode cell that comprises a test electrode, a current source electrode, and a reference electrode, and wherein said test electrode comprises a microelectrode that has a radius of not more than about 5 μm.

10. The process analyzer of claim 6, comprising at least one analytical module selected from the group consisting of Pulsed Cyclic Galvanostatic Analysis (PCGA) modules, spectroscopy modules, potentiometry modules, and Karl Fischer coulometry modules.

11. The process analyzer of claim 10, comprising a Pulsed Cyclic Galvanostatic Analysis (PCGA) module, wherein said PCGA module comprises a microelectrode that has a radius of not more than about 5 μm.

12. The process analyzer of claim 6, wherein the primary manifold comprises one or more variable volume displacement pumps.

13. The process analyzer of claim 6, wherein the primary manifold comprises one or more face-sealed valves.

14. The process analyzer of claim 6, wherein the primary manifold comprises one or more two-way valves and/or three-way valves.

15. The process analyzer of claim 6, wherein the primary manifold comprises a make/break plate having pre-manufactured fluid pathways thereon.

16. The process analyzer of claim 6, wherein the one or more analytical modules are controlled by one or more microcontrollers, and wherein the primary manifold comprises a serial port for connecting said microcontrollers with the computational device, so as to enable communicative association therebetween.

17. The process analyzer of claim 16, wherein the primary manifold comprises one or more variable volume displacement pumps, onto which said serial port is attached.

18. The process analyzer of claim 6, wherein the computation device outputs the collected and processed analytical data to a central control network.

19. A process analyzer for analyzing composition of sample electrochemical deposition solutions, said process analyzer comprising at least one microelectrode having a radius of not more than about 5 μm, wherein the microelectrode has a composite structure, including an inner electrically conductive metal core, and an outer dielectric layer formed by oxidization of a metal or metal alloy including at least one metal selected from the group consisting of tantalum, niobium, zirconium, hafnium, and titanium.

20. A process analyzer for analyzing composition of sample electrochemical deposition solutions, said process analyzer comprising:
  at least one microelectrode having a radius of not more than about 5 μm, having a composite structure including an inner electrically conductive metal core, and having an outer dielectric layer formed by oxidization of a metal or metal alloy including at least one metal selected from the group consisting of tantalum, niobium, zirconium, hafnium, and titanium;

one or more analytical modules for analyzing fluid samples;

a primary manifold communicatively connected to said one or more analytical modules for introducing fluid samples thereinto, the manifold comprising at least one of (i) one or more variable volume displacement pumps; (ii) one or more face-sealed valves; (iii) one or more two-way valves and/or three-way valves, and (iv) a make/break plate having pre-manufactured fluid pathways thereon; and a computational device communicatively associated with said one or more analytical modules for collecting and processing analytical data therefrom.

* * * * *